(12) United States Patent
Moon et al.

(10) Patent No.: US 11,638,684 B2
(45) Date of Patent: May 2, 2023

(54) PUMP-TYPE TOOTHPASTE COMPOSITION

(71) Applicant: LG HOUSEHOLD & HEALTH CARE LTD., Seoul (KR)

(72) Inventors: Kyo-Tae Moon, Seoul (KR); Ji-Hye Lee, Seoul (KR); Aram You, Seoul (KR); Seong-Lok Hwang, Seoul (KR); Won-Ho Ha, Seoul (KR)

(73) Assignee: LG HOUSEHOLD & HEALTH CARE LTD., Seoul (KR)

(*) Notice: Subject to any disclaimer, the term of this patent is extended or adjusted under 35 U.S.C. 154(b) by 0 days.

(21) Appl. No.: 16/760,312

(22) PCT Filed: Oct. 16, 2018

(86) PCT No.: PCT/KR2018/012198
§ 371 (c)(1),
(2) Date: Apr. 29, 2020

(87) PCT Pub. No.: WO2019/088512
PCT Pub. Date: May 9, 2019

(65) Prior Publication Data
US 2020/0253854 A1 Aug. 13, 2020

(30) Foreign Application Priority Data

Oct. 30, 2017 (KR) .................. 10-2017-0142628
Oct. 31, 2017 (KR) .................. 10-2017-0143952

(51) Int. Cl.
*A61K 8/81* (2006.01)
*A61K 8/04* (2006.01)
*A61Q 11/00* (2006.01)

(52) U.S. Cl.
CPC ............ *A61K 8/8147* (2013.01); *A61K 8/042* (2013.01); *A61Q 11/00* (2013.01); *A61K 2800/48* (2013.01); *A61K 2800/87* (2013.01); *A61K 2800/92* (2013.01)

(58) Field of Classification Search
CPC ............ A61Q 11/00; A61K 8/86; A61K 8/21
USPC ........................................... 424/49
See application file for complete search history.

(56) References Cited

U.S. PATENT DOCUMENTS

| | | | |
|---|---|---|---|
| 2,792,856 A * | 5/1957 | Coppage | A47K 5/18 141/362 |
| 5,178,869 A * | 1/1993 | Ebine | A61K 8/4926 222/192 |
| 6,136,298 A | 10/2000 | Gaffar et al. | |
| 6,187,292 B1 | 2/2001 | Amiche et al. | |
| 8,956,593 B2 * | 2/2015 | Burgess | A61K 8/24 424/49 |
| 2001/0033846 A1 | 10/2001 | Roulier et al. | |
| 2001/0037750 A1 * | 11/2001 | Miyama | A61K 6/20 106/35 |
| 2004/0101493 A1 | 5/2004 | Scott et al. | |
| 2005/0207994 A1 * | 9/2005 | Sugiyama | A61K 8/345 424/49 |
| 2007/0053851 A1 * | 3/2007 | Maillan | A61K 8/498 424/729 |
| 2008/0305168 A1 | 12/2008 | Moon et al. | |
| 2012/0244203 A1 * | 9/2012 | Sakamoto | A61K 8/0241 424/401 |
| 2014/0086851 A1 * | 3/2014 | Fisher | A61K 8/19 424/57 |
| 2015/0044161 A1 * | 2/2015 | Chuang | A01N 43/36 526/264 |
| 2016/0151255 A1 | 6/2016 | You et al. | |

FOREIGN PATENT DOCUMENTS

| | | | | |
|---|---|---|---|---|
| CN | 1988876 A | 6/2007 | | |
| CN | 106890103 A | 6/2017 | | |
| EP | 2 100 590 A1 | 9/2009 | | |
| JP | 2000-191484 A | 7/2000 | | |
| KR | 95-16691 A | 7/1995 | | |
| KR | 100129819 B1 | 11/1997 | | |
| KR | 10-2000-0011873 A | 2/2000 | | |
| KR | 10-0239315 B1 | 2/2000 | | |
| KR | 10-2000-0016390 A | 3/2000 | | |
| KR | 10-2005-0086796 A | 8/2005 | | |
| KR | 10-0731892 B1 | 6/2007 | | |
| KR | 10-2009-0076441 A | 7/2009 | | |
| KR | 10-2009-0086433 A | 8/2009 | | |
| KR | 10-2012-0084499 A | 7/2012 | | |
| KR | 10-2014-0146983 A | 12/2014 | | |
| KR | 10-2015-0045166 A | 4/2015 | | |
| KR | 10-2015-0111649 A | 10/2015 | | |
| KR | 10-2016-0131488 A | 11/2016 | | |
| WO | WO 02/092028 | * | 11/2002 | ............ A61K 7/00 |
| WO | WO 2011/053291 A1 | 5/2011 | | |
| WO | WO 2014/204221 A1 | 12/2014 | | |
| WO | WO 2015/016057 A1 | 2/2015 | | |

OTHER PUBLICATIONS

International Search Report for PCT/KR2018/012198 dated Jan. 25, 2019.

* cited by examiner

*Primary Examiner* — Walter E Webb
(74) *Attorney, Agent, or Firm* — Birch, Stewart, Kolasch & Birch, LLP

(57) ABSTRACT

The present disclosure relates to a pump-type toothpaste composition which can be provided by being comprised in a pump-type container, and particularly, relates to a pump-type toothpaste composition with improved feeling of use when brushing teeth. In addition, the present disclosure relates to a pump toothpaste composition having improved tailing and dry-hardening property. The pump-type toothpaste composition of the present disclosure may comprise a hydrocolloid.

15 Claims, No Drawings

PUMP-TYPE TOOTHPASTE COMPOSITION

TECHNICAL FIELD

The present application claims priority based on Korean application No. 10-2017-0142628 filed on Oct. 30, 2017, and Korean application No. 10-2017-0143952 filed on Oct. 31, 2017, and all the contents disclosed in the specification and drawings of the corresponding applications are incorporated in the present application.

The present disclosure relates to a toothpaste composition, which is to be comprised in a pump-type container, wherein viscosity of the toothpaste composition is increased by saliva, and thereby providing improved feeling of use.

In addition, the present disclosure relates to a pump toothpaste composition with improved tailing and dry-hardening properties.

Commonly used toothpaste compositions for cleansing of mouth and teeth are distributed as paste, powder, gel/mucus or liquid products, and there are certain advantages and disadvantages to their use and handling.

The paste-type toothpaste firstly developed by U.S. Colgate company has been sold by being comprised in an aluminum tube, and this aluminum tube was still used until the 1970s. The development of the container of the paste-type toothpaste as a laminated film material of aluminum as in modern times is achieved by development of polymers and polymer processing technology. However, it is a reality that such a tube-type toothpaste has many inconveniences in that it has high viscosity and has a high possibility to cause damages of tooth enamel layers by its abrasive component, and it is inconvenient to squeeze when using, and also it is impossible to completely use products in a container and therefore there is residual toothpaste in a container to be discarded, and it causes environmental pollution. In order to improve the releasability of such toothpaste and the like, a liquid toothpaste product having the flowing property in a plastic container has been developed, but when it flows too well, it is difficult to effectively deliver a drug in the toothpaste product to teeth and gums. Accordingly, it has been widely used as an oral gargle that performs functions of inhibiting oral bacteria and removing bad breath, but it could not exhibit an effect of sufficient brushing such as removal of plaque in oral cavity and removal of oral bacteria and the like due to a problem of lack of cleaning ingredients and easy flow. There has been an attempt to apply a vacuum pumping type of plastic container to discharge high viscosity of paste, which has been applied next in order to enhance the user convenience, and some products are on the market, but they have price problems and poor releasability of conventional paste toothpastes and the like. In addition, powders are inconvenient in use since their particles are sprayed or scattered during its use. Furthermore, liquid-type dip tube pump toothpaste is on the market, and the releasability is improved by low viscosity, but it does not provide viscous feeling of use provided in paste toothpaste.

On the other hand, pump toothpaste comprised in a plastic container was released to solve disadvantages of the tube-type toothpaste, but one of the problems of the pump toothpaste is tailing, and due to this, there is a problem that the container is dirty or the shape retention of the toothpaste on the toothbrush is poor.

In addition, conventional tube-type toothpaste commonly comprises sorbitol as a lubricant and a moisturizer, but sorbitol is used in an aqueous solution of about 70%, and has a property of rapidly converting into solid as water is dried, and in particular, it contains solids as an abrasive, and therefore it can be easily solidified upon contact with air. In particular, pump toothpaste is required to improve dry-hardening property of the pump toothpaste composition itself, since contact with air is inevitable by applying a pump-type container to toothpaste.

Numerous references are cited throughout the present specification, and the quotation is marked. The disclosure contents of the cited references are incorporated by reference in the present specification, and the level of the technical field to which the present disclosure belongs and the contents of the present disclosure are more clearly described.

DISCLOSURE

Technical Problem

Accordingly, a problem to be solved by the present disclosure is to solve the aforementioned problems and provide a pump-type toothpaste composition which is to be comprised in a pump-type container.

In addition, it is to provide a pump-type toothpaste composition, which is a toothpaste composition with improved feeling of use of toothpaste as the viscosity is increased by saliva or water when brushing teeth.

Furthermore, it is to provide a pump-type toothpaste composition, which is a toothpaste composition with improved dry-hardening phenomena of contents when discharging.

Moreover, it is to provide a pump-type toothpaste composition, which is a toothpaste composition with improved tailing and dry-hardening properties.

Other objects and advantages of the present disclosure will become more apparent by the following detailed description of the invention, claims and drawings.

Technical Solution

One aspect of the present disclosure is to provide a pump-type toothpaste composition which can be provided by being comprised in a pump-type container to solve the above problems. More specifically, the present disclosure provides a pump-type toothpaste composition, which is a toothpaste composition with improved feeling of use of toothpaste by increasing viscosity by saliva or water when brushing teeth. In addition, it provides a pump-type toothpaste composition, which is a toothpaste composition with improved dry-hardening of contents when discharging.

Hereinafter, it will be described in more detail.

For the pump-type toothpaste composition, it is required to solve a problem of dry-hardening of contents when discharging, due to expression of solids in contents as water contained in the composition is evaporated. In addition, it is need to solve a problem that richness provided in conventional paste toothpaste cannot be provided as the toothpaste is more diluted by saliva in mouth when brushing teeth.

Accordingly, the present inventors have found that there is an effect of providing rich feeling of use, as the hydrocolloid is swelled by water or saliva when brushing teeth, when the content of water is lowered and a non-hydrated hydrocolloid is comprised, in a pump-type toothpaste composition comprised in a pump-type container, thereby completing the present disclosure.

In the specification according to the present disclosure, the term 'pumping type' means a structure capable of releasing contents stored inside of a container to the outside through a discharge port by pump action using a pushing member of the container. Specifically, it means a structure of releasing a toothpaste composition inside of a container to the outside of the container through pump action of a piston to use, and in other words, by the pump action, contents can be released from the inner bottom of the container to the outside by a piston equipped inside of the container.

As the pump used in the pump-type container of the present disclosure, for example, a dip pump (dip tube pump), E-sensor pump, oil pump, foaming pump, mist pump or the like may be used, and preferably, a dip tube pump may be used.

The dip tube pump is positioned deeply inside of a pouch-type container of which outer packaging container is a fixed type or container can be modified, and therefore it pulls contents from the bottom of the container to the top and discharge them, and its use is convenient due to soft feeling when pumping and accurate and various discharging amounts, and actions of the internal structure according to viscosity of contents, and it is commonly used in shampoo or bodywash products. The dip tube pump may be installed in a fixed-type outer packaging container or may be installed in a deformable container, and in the former case, contents may be directly comprised in the outer packaging container, and in the latter case, a deformable pouch is additionally included inside of the outer packaging and contents are comprised inside of the pouch, and therefore it may be in a form that the inner pouch is reduced by depressurization as contents are reduced.

The 'E-sensor pump' has an advantage capable of minimizing and refining the discharging amount. The 'oil pump' is a pump which is effective when comprising contents which may cause leakage during use. The 'foaming pump' is a pump having an advantage capable of producing rich foam only by the internal structure of the pump without using Freon gas. The 'mist pump' is a pump in a structure spraying contents in a fine particle form.

In the specification of the present disclosure, the term 'substantially non-hydrated hydrocolloid' was used as a concept including a hydrocolloid in which the hydrocolloid is dissolved in a supersaturated state in a composition and is not hydrated by water.

Specifically, the present disclosure provides a pump-type toothpaste composition comprised in a pump-type container, which is a pump-type toothpaste composition that comprises a hydrocolloid and water, wherein the weight ratio of the hydrocolloid and water is 0.5-10:1 (hydrocolloid:water), preferably, 0.8-5:1. When the weight ratio is 0.5-10:1, a pump-type toothpaste composition comprising a substantially non-hydrated hydrocolloid can be provided.

Preferably, the content of water is less than 5% by weight based on the total weight of the composition, and more preferably, it is 0.001 to less than 5% by weight based on the total weight of the composition; and the content of the hydrocolloid is 0.1 to 15% by weight based on the total weight of the composition, and more preferably, it is 3 to 6% by weight. When the content of water is less than 0.001% by weight, a problem in stability of the formulation may be caused, and when it is over 5% by weight, a problem that the object of the present disclosure may be not solved may be caused. In addition, when the content of the hydrocolloid is 0.1 to 15% by weight based on the total weight of the composition, the 'substantially non-hydrated hydrocolloid' of the present disclosure may be comprised.

As the water comprised in the present disclosure, water used for toothpaste compositions in the art may be used, and for example, purified water; and plant extract of aloe vera, Witch Hazel, hamamelis, cucumber, lemon, lavender, rose, and the like, but not limited thereto.

The 'abrasive' comprised herein is a substance functioning of removing oral plaque, and it is necessarily used for increasing the efficiency of removal of dental plaque and removing hard foreign substances and the like, and Mohs hardness represents a value of about 3-6. Herein, a piston of the pump container is produced by low-density polyethylene, and the hardness of the polyethylene is lower than the hardness of the abrasive used, and therefore the pump may be worn out, and thus it is preferable to comprise an abrasive in a small amount. In one embodiment, the abrasive may be comprised in an amount of 0.1 to 50% by weight, preferably, 1 to 20% by weight, based on the total weight of the composition. In other embodiment, the abrasive may be comprised in an amount of 30% by weight or less, preferably, 0.5 to 20% by weight, based on the total weight of the composition.

For example, the abrasive may comprise any one selected from the group consisting of calcium monohydrogen phosphate, precipitated silica, fumed silica, hydrated silicon dioxide, colloidal silicon dioxide, silica gel, zeolite, calcium carbonate, hydrated alumina, kaolin, cellulose and a mixture thereof, but not limited thereto.

The foaming agent comprised in the present disclosure may be used to make formation of foam easy, and as one example, a single or two kinds or more of anion, amphoteric and non-ionic surfactants such as sodium alkyl sulfate, sodium lauryl sulfate, alkyl sarcosinate, lauryl sarcosinate, sodium cocoyl glutamate, sodium myristoyl glutamate, cocamidopropyl betaine, sucrose fatty acid ester, sorbitan fatty acid ester, copolymer of polyoxyethylene polyoxypropylene (poloxamer), and the like may be mixed and used. In addition, as other example, as the foaming agent, an anion surfactant such as sodium lauric acid, sodium palmitic acid, sodium alkyl sulfate, sodium lauryl sulfate, potassium lauryl sulfate, POE-lauryl sulfate triethanolamine, POE-sodium lauryl sulfate, sodium lauroyl sarcosine, N-myristoyl-N-sodium methyl taurine, coconut oil fatty acid sodium methyltauride, sodium lauryl methyltauride, POE-sodium oleyl ether phosphate, POE-stearyl ether phosphate, sodium di-2-ethylhexyl sulfosuccinate, sodium monolauroyl monoethanolamide polyoxyethylene sulfosuccinate, sodium lauroyl polypropylene glycol sulfosuccinate, linear sodium dodecyl benzene sulfonate, linear dodecyl benzene sulfonate triethanolamine, linear dodecyl benzene sulfonate, hardened coconut oil fatty acid sodium glycerin sulfate, monosodium N-lauroyl glutamate, disodium N-stearoyl glutamate, monosodium N-myristoyl-L-glutamate, and the like; a non-ionic surfactant such as sorbitan monooleate, sorbitan monoisostearate, sorbitan monolaurate, sorbitan monopalmitate, sorbitan monostearate, sorbitan sesquioleate, sorbitan trioleate, penta-2-ethylhexyl acid diglycerol sorbitan, tetra-2-ethylhexyl acid diglycerol sorbitan, mono cottonseed oil fatty acid glycerin, monoerucic acid glycerin, sesquioleic acid glycerin, monostearate glycerin, $\alpha,\alpha'$-oleic acid pyroglutamate glycerin, monostearate glycerin malate, POE-sorbitan monooleate, POE-sorbitan monostearate, POE-sorbitan tetraoleate, POE-sorbit monolaurate, POE-sorbit monooleate, POE-sorbit pentaoleate, POE-sorbit monostearate, and the like; a cationic surfactant such as stearyl trimethylammonium chloride, lauryl trimethylammonium chloride, cetyl pyridinium chloride, N,N'-dimethyl-3,5-methylene piperidinium, alkyl quaternary ammonium, alkyl dimethyl benzyl ammonium, alkyl isoquinolinium, dialkyl morphonium, benzalkonium chloride, benzethonium chloride, and the like; an amphoteric surfactant such as sodium 2-undecyl-N,N,N-(hydroxyethylcarboxymethyl)-2-imidazoline, 2-cocoyl-2-imidazolinium hydroxide-1-carboxyethyloxy disodium, 2-heptadecyl-N-carboxymethyl-N-hydroxyethylimidazolinium betaine, lauryl dimethylamino acetate betaine, alkyl betaine, amide betaine, sulfobetaine, and the like; or a mixture thereof may be used in an amount of 1 to 20% by weight, based on the total weight of the composition, but not limited thereto.

The composition of the present disclosure comprises the 'non-hydrated hydrocolloid' as a thickener, and the hydrocolloid preferably comprise a water-swelling colloid. The composition comprises a 'non-hydrated' hydrocolloid in the composition, and the hydrocolloid has a characteristic of being swelled when contacting with water and increasing the viscosity of the composition.

In addition, the composition of the present disclosure may provide a pump-type toothpaste composition with viscosity of 4,000 cP to 35,000 cP, preferably, 5,000 to 30,000 cP, at a room temperature (25° C.). The viscosity may be measured by various methods known in the art, and for example, it may be measured by rotating at a rotation speed of 20 revolutions per minute using a Brookfield viscometer spindle No. 5 or 7, but not limited thereto. When the viscosity of the composition is 4,000 to 35,000 cP, it may be not hardened and have excellent discharging and also have excellent viscosity when brushing teeth.

Furthermore, the present disclosure may provide a pump-type toothpaste composition with increasing viscosity when brushing teeth. The non-hydrated hydrocolloid comprised in the present disclosure increases the viscosity of the toothpaste composition, thereby providing rich feeling of use, when diluted by water or saliva added when brushing teeth.

In one example, the present inventors have confirmed that the viscosity is increased 1.1 to 2 times compared to the viscosity before dilution, when the toothpaste composition according to the present disclosure of 10 g and 1ml purified water are added and mixed.

In addition, the hydrocolloid comprised in the present disclosure may use agarose, agar, cellulose, dextrin, gelatin, Japanese agar, pectin, starch, chemically modified starch, carboxymethyl cellulose, methyl cellulose, sodium carboxymethyl cellulose, polyvinyl pyrrolidone, hydroxyproprylmethyl cellulose, hydroxymethyl cellulose, hydroxyethyl cellulose, hydroxypropyl cellulose, methylhydroxypropyl cellulose, carbomer, galactomannan, glucomannan, carrageenan, gum, locust bean gum, gellan gum, xanthan gum, gum karaya, gum Arabic, gum tragacanth, guar gum, acrylic polymer, alginate, or a mixture thereof, and preferably, sodium carboxymethyl cellulose, carrageenan, acrylic polymer, xanthan gum or a mixture thereof may be used.

The method for preparing the toothpaste composition of the present disclosure may prepare it by common preparation methods in the art, for example, it may be provided in a gel form.

In the specification according to the present disclosure, the term 'gel' is used as a concept to distinguish between conventional liquid toothpaste in a dilute form and a high viscosity of paste toothpaste. The gel is a formulation to be distinguished from the conventional liquid formulation, and means a formulation having a greater degree of stickiness than the liquid composition and is viscous. The gel composition of the present disclosure means a formulation having elasticity and rigidity than the liquid composition. In addition, the gel composition of the present disclosure has fluidity due to lower viscosity than a paste type of toothpaste and can easily discharge contents to the outside due to flowability, and can form foam with appropriate viscosity when discharging.

In the specification according to the present disclosure, the term 'elasticity' means a property that an object deformed by an external force tries to return to its original shape when the force is removed, and it has been used as a broad concept meaning a property of an object that is intended to maintain its original form. In other words, it has been used as a broad meaning including all properties to intend to maintain the original shape after discharging a toothpaste composition from a discharge port.

The pump-type toothpaste composition according to the present disclosure may further comprise other additives commonly used for toothpaste compositions in the art, according to its formulation and purpose of use, to the extent that the object of the present disclosure is not impaired. As the other additives, for example, a lubricant, a flavoring, a sweetener, a pharmaceutical agent, a pigment, a pH adjusting agent, a preservative, and a whitening agent, and the like may be further comprised.

Preferably, the toothpaste composition according to the present disclosure is provided as a pump-type toothpaste composition, and therefore, in order to prevent clogging of the discharge port due to drying, it is preferable to comprise a lubricant (polyol, glycerin, etc.).

The lubricant means a substance acting to reduce friction between two sides sliding in contact with each other, and the lubricant lubricates, thereby playing a role in preventing abrasion of a piston by a raw material (solid such as an abrasive) showing wear properties contained in the toothpaste composition of the present disclosure. The lubricant may comprise for example, any one selected from the group consisting of polyethylene glycol, glycerol, propylene glycol, ethylene glycol, polypropylene glycol and a mixture thereof, but not limited thereto. Preferably, it may comprise any one selected from the group consisting of polyethylene glycol 200 to 600, glycerol, propylene glycol, ethylene glycol, polypropylene glycol and a mixture thereof. Preferably, as a liquid lubricant, petroleum oil, animal and vegetable oil, synthetic lubricating oil, and the like may be used, and most preferably, in an aspect of stability and excellent usability of the composition, glycerin may be used. Otherwise, the lubricant is not limited to glycerin, and it may include a polyol of high molecular weight which can be present in a solid state at a room temperature by intramolecular interaction over a certain molecular weight, but can be liquefied by controlling the preparation temperature and can be maintained in a stable state when manufactured, such as polyethylene glycol or polypropylene glycol in a polymer form.

The lubricant may be comprised in a content of 30 to 85% by weight based on the total composition.

In the composition of the present disclosure, a fragrance ingredient and a sweetener may be added to consumers' preference.

The fragrance ingredient remains in the oral cavity and allows to maintain a sense of freshness by continually emitting fragrances. As the fragrance ingredient, mint like peppermint, spearmint, etc., wintergreen, methyl salicylate, eugenol, melon, strawberry, orange, vanillin, or the like may be used. In general, the fragrance ingredient may be used in a range of 0.001 to 10% by weight based on the total weight of the composition.

The sweetener may play a role in sustaining occurrence of saliva by providing the taste continuously while remaining in the oral cavity, and it may be added to overcome basic tastes of the formulation of the composition. As the sweetener, one kind of saccharin, sucralose, sugar, xylitol, sorbitol, lactose, mannitol, maltitol, erythritol, aspartame, taurine, saccharin salt, D-tryptophan, and the like, or a mixture thereof may be used. Among saccharin salts, sodium saccharin is most widely used. The amount of the sweetener is generally in a range of 0.001 to 20% by weight based on the total weight of the composition.

As the pharmaceutical agent used for oral hygiene, ingredients having an effect of cavity prevention, gum disease prevention, plaque deposition prevention, whitening, or the like may be used. The pharmaceutical agent used for cavity prevention includes a compound approved as a safe substance by U.S. Food and Drug Administration, including fluoride ion. The compound which can be used as a source of the fluoride ion includes sodium fluoride, sodium monofluorophosphate, stannous fluoride, and ammine fluoride. The content of fluorine may differ in usage depending on countries, but preferably, it is common to use a mixture of 1 kind or 2 kinds or more of sources so as to have a fluorine ion concentration in a range of 850 to 1500 ppm. A recalcification agent may also act as a cavity preventing agent. The recalcification plays a role in regenerating and restoring hydroxyapatite that is a major component of teeth. The major component of hydroxyapatite consists of divalent calcium cation and phosphate anion. Accordingly, one which provides a calcium ion and a phosphate ion simultaneously or contains a calcium divalent ion or one kind or more of phosphate anions so as to shift oral chemical equilibrium towards the formation of hydroxyapatite may be used as the recalcification agent.

The substance providing calcium and phosphorus includes raw material hydroxyapatite, dicalcium phosphate, calcium chloride, casein phospeptide, calcium glycerophosphate, monosodium phosphate, sodium diphosphate, sodium triphosphate, monopotassium phosphate, dipotassium phosphate, tripotassium phosphate, or the like. Generally, it is preferable to use the recalcification agent in a range of 0.001 to 20% by weight based on the total composition. When it is less than 0.001% by weight, the recalcification effect is reduced, and when it is more than 20% by weight, properties which the formulation originally has are lost. One of purposes of using an oral hygiene item is to alleviate a proceeding gum disease, as well as, to prevent a gum disease in advance, by sterilization or anti-inflammation action against harmful microorganisms present in the oral cavity. For this purpose, isopropyl methyl phenol, cyclohexidin, cetyl pyridinium chloride, triclosan, xanthorrhizol, or the like, which is known as an antimicrobial agent, may be used, and for anti-inflammation action, vitamins and enzymes, allantoin and its derivative and the like may be used. The pharmaceutical agent may be contained in an amount of 0.005% by weight to 5% by weight. When the content of the pharmaceutical agent is less than 0.005, it is difficult to show a medicinal effect, and when it is contained more than 5% by weight, there is a disadvantage of changing the taste of the basic base. Peroxide, carbamide peroxide, calcium peroxide or the like, which shows a whitening effect in addition to gum diseases, may be used, and to obtain a plaque deposition inhibition effect, sodium pyrophosphate, acidic sodium pyrophosphate, potassium pyrophosphate, sodium metaphosphate, or the like is used. In general, this pharmaceutical agent is used in a range of 0.001 to 10% by weight based on the total weight of the composition.

If the pigment is a pigment generally used for toothpaste, it is not particularly limited by the particle structure, such as particle diameter, porous, non-porous, and the like. For example, white inorganic pigments such as titanium oxide, cerium oxide, barium sulfate, and the like; color inorganic pigments such as iron oxide, carbon black, titanium.titanium oxide sinter, chrome oxide, chrome hydroxide, deep blue, navy blue, and the like; organic pigments such as organic pigment powders including red 201, red 202, red 205, red 226, red 228, orange 203, orange 204, blue 404, yellow 401, etc., zirconium, barium or aluminum lakes including red 3, red 104, red 106, orange 205, yellow 4, yellow 5, green 3, blue 1, etc., and the like; metal powders such as aluminum powder, gold powder, silver powder, and the like; indirect pigments such as titanated mica, titanated barium sulfate, and titanated silica and the like may be used.

As the pH adjusting agent, phosphate, sodium phosphate, citrate, sodium citrate, succinate, sodium succinate, tartrate, sodium tartrate, or the like may be used, and the acidity of an oral composition is generally 5 to 8.

As the preservative, benzoic acid, methyl paraben, propyl paraben, sodium benzoate or the like may be used.

As the whitening agent, titanium oxide is used, and generally, it is used in an amount of 0.1% to 2% by weight based on the total weight of the composition.

In addition, the present disclosure may provide a pump-type toothpaste composition consisting of an abrasive of 1 to 50% by weight, a foaming agent of 1 to 20% by weight, a hydrocolloid of 0.1 to 30% by weight, and the remaining amount of other additives.

Furthermore, the toothpaste composition of the present disclosure may comprise water of less than 5% by weight based on the total weight of the composition, and the water may be hydrated with components other than the hydrocolloid comprised in the present disclosure, and the content of water participating in hydration with the components other than the hydrocolloid may be 0.1 to 30 parts by weight, particularly, 1 to 20 parts by weight based on 100 parts by weight of water. When the content of water participating in hydration with the components other than the hydrocolloid is 0.1 to 30 parts by weight based on 100 parts by weight of water, in addition to ensuring the stability of the formulation, it is possible to provide a toothpaste composition comprising a substantially non-hydrated hydrocolloid.

The method for preparing a toothpaste composition of the present disclosure may prepare it by common preparation methods in the art.

The toothpaste composition according to the present disclosure may be diverted into mouthwash, a denture cleansing agent, or the like.

The present disclosure provides pump-type toothpaste comprising the pump-type toothpaste composition and a pump-type container comprising the pump-type toothpaste composition, and when using the pump-type toothpaste, excellent richness is exhibited.

In the specification according to the present disclosure, the term 'richness' refers to a sense of fullness in the mouth, by increasing the viscosity by a hydrocolloid swelled by saliva that occurs during brushing teeth.

Other aspect of the present disclosure provides a pump-type toothpaste composition comprised in a pump-type container, which is a pump-type toothpaste composition comprising an acrylic polymer and a hydrocolloid.

The present inventors have tried to solve problems of tailing and hardening due to contact with air (dry-hardening), which are problems of the pump-type toothpaste. As a result, they have found that when acrylic polymer and hydrocolloid components are comprised simultaneously, tailing and dry-hardening are improved, and also a physical property capable of being discharged through a pump by being comprised in a pump-type container, thereby completing the present disclosure.

It may be a polyacrylic polymer, a polymethacrylic polymer, a polyalkylacrylic polymer, or a polyalkylmethacrylic polymer, comprised in the pump-type toothpaste composition of the present disclosure.

The acrylic polymer is one form of vinyl polymers, and may be prepared from an acrylic monomer, and as the acrylic monomer, ester containing a vinyl group, that is, that two carbons are combined by a double bond and a carbonyl group is directly combined to one of these carbons (alpha carbon), may be used.

More specifically, the acrylic polymer used in the present disclosure may be prepared by polymerizing one or more kinds of monomers selected from the group consisting of acrylate, methacrylate, alkyl acrylate, alkyl methacrylate, hydroxyalkyl acrylate, hydroxyalkyl methacrylate, diethylene glycol acrylate, diethylene glycol methacrylate, acrylamide, methacrylamide, diacetone acrylamide, methylol acrylamide, and methylol methacrylamide, (meth)acrylic ester monomer having an alkyl group of 1 to 20 carbon atoms, methyl(meth)acrylate, ethyl(meth)acrylate, propyl(meth)acrylate, butyl(meth)acrylate, hexyl(meth)acrylate, 2-ethyl hexyl(meth)acrylate, lauryl(meth)acrylate, stearyl (meth)acrylate, octadecyl(meth)acrylate, isooctyl(meth) acrylate, isononyl(meth)acrylate, isodecyl(meth)acrylate, and isobonyl(meth)acrylate, but not merely limited thereto.

The acrylic polymer used in the present disclosure is preferably present alone without containing other components such as a flavoring agent, and the like inside it, and also, the acrylic polymer is required to be not cross-linked substantially.

The pump-type toothpaste composition of the present disclosure should be discharged when used by being comprised in a pump container, but when using a cross-linked acrylic polymer, the solubility is reduced, and thereby a problem that may not be discharged may occur. Like this, a hydrocolloid with high elasticity is used as a basic base, and an acrylic polymer is added thereto, and thereby the ratio of elasticity and viscosity may be adjusted to reduce tailing property of the toothpaste composition.

Specific kinds and examples of the hydrocolloid are described above.

In the composition of the present disclosure, the components may be comprised so that the weight ratio of the acrylic polymer to the hydrocolloid is 0.05 to 20.

As one example, the pump-type toothpaste composition of the present disclosure may comprise the acrylic polymer of 0.05 to 1.0% by weight and the hydrocolloid of 0.05 to 1.0% by weight.

The toothpaste composition according to the present disclosure may further comprise components commonly used for toothpaste compositions in the art, an abrasive, a lubricant, a flavoring, a sweetener, a pharmaceutical agent, a pH adjusting agent, a preservative, a bonding agent, a foaming agent, a whitening agent, and the like, other than a bonding agent, according to its formulation and purpose of use. The detailed description for these additional components is described above.

The pump-type toothpaste composition of the present disclosure is characterized in that the residual length of remaining toothpaste in a discharge port after pumping is reduced 50% or more, preferably, 70% or more, more preferably, 90% or more, compared to the case of not comprising an acrylic polymer.

In addition, the toothpaste composition of the present disclosure may have a strain rate of 1% or more, preferably 3% or more, more preferably 5% or more, and a recovery rate of 40% or more, preferably 60% or more, more preferably 80% or more, when applying a force of 4 Pa.

The present disclosure also provides pump-type toothpaste comprising the aforementioned pump-type toothpaste composition and a pump-type container comprising the pump-type toothpaste composition.

The pump-type container means a structure capable of releasing contents stored inside of a container to the outside through a discharge port by pump action using a pushing member of the container. Specifically, it means a structure of releasing a toothpaste composition inside of a container to the outside of the container through pump action of a piston to use, and in other words, by the pump action, contents can be released from the inner bottom of the container to the outside by a piston equipped inside of the container.

Such a pump-type toothpaste of the present disclosure may be diverted into mouthwash, a denture cleansing agent, or the like.

Advantageous Effects

According to the present disclosure, a pump-type toothpaste composition which can be comprised in a pump-type container is provided, and in particular, the pump-type toothpaste composition has an effect of exhibiting excellent feeling of use providing viscosity to toothpaste by saliva when brushing, as well as an effect of improving dry-hardening phenomena of contents when discharging.

In addition, the present disclosure provides a pump-type toothpaste composition which can be provided by being comprised in a pump-type container and pump-type toothpaste comprising the same, and in particular, it has an effect of improving tailing and dry-hardening property of toothpaste.

DETAILED DESCRIPTION OF THE EMBODIMENTS

Hereinafter, in order to help understanding of the present disclosure, it will be described in detail by examples, and the like. However, the examples according to the present disclosure may be modified into various other forms, and the scope of the present disclosure should not be construed to be limited by the following examples. The examples of the present disclosure are provided to illustrate the present disclosure to those skilled in the art more completely.

I. Preparative Example A of Pump-Type Toothpaste Composition

Preparation of Examples A1-A6 and Comparative Examples A1-A3

Toothpaste compositions of Examples and Comparative examples were prepared by components and weights shown in the following Table 1. Toothpaste compositions were prepared by completely distributing purified water, glycerin, a flavoring, a pharmaceutical agent, a surfactant, a hydrocolloid, and powder components such as sodium saccharin, and the like and primarily mixing them, and then adding an abrasive such as precipitated silica, and the like, and other components and mixing them under a vacuum condition.

TABLE 1

|  | Example A1 | Example A2 | Example A3 | Example A4 | Example A5 | Example A6 | Comparative example A1 | Comparative example A2 | Comparative example A3 |
|---|---|---|---|---|---|---|---|---|---|
| Precipitated silica | 15.00 | 15.00 | 15.00 | 15.00 | 15.00 | 15.00 | 15.00 | 15.00 | 15.00 |
| Glycerin | 74.00 | 73.00 | 72.00 | 71.00 | 71.00 | 71.00 | 75.00 | 74.00 | 74.00 |
| Sodium lauryl sulfate | 2.00 | 2.00 | 2.00 | 2.00 | 2.00 | 2.00 | 2.00 | 2.00 | 2.00 |
| Sodium saccharin | 0.20 | 0.20 | 0.20 | 0.20 | 0.20 | 0.20 | 0.20 | 0.20 | 0.20 |
| Cellulose gum | 3.00 | 4.00 | 5.00 | 3.00 | 3.00 | 3.00 | 1.00 | 1.00 | |
| Acrylic polymer | | | | | 3.00 | 1.00 | | | |
| Xanthan gum | | | | 3.00 | | 2.00 | 1.00 | 1.50 | 2.50 |
| Sodium fluoride | 0.22 | 0.22 | 0.22 | 0.22 | 0.22 | 0.22 | 0.22 | 0.22 | 0.22 |
| Vitamin E | 0.20 | 0.20 | 0.20 | 0.20 | 0.20 | 0.20 | 0.20 | 0.20 | 0.20 |
| Flavoring | 1.00 | 1.00 | 1.00 | 1.00 | 1.00 | 1.00 | 1.00 | 1.00 | 1.00 |
| Purified water | 4.38 | 4.38 | 4.38 | 4.38 | 4.38 | 4.38 | 4.38 | 4.88 | 4.88 |

Experiment 1. Evaluation of Dry-Hardening of Toothpaste

After filling Examples and Comparative examples prepared above in 24 well plates, they were dried in a dried oven furnace of 60° equipped with a fan for 48 hours. Then, dry-hardening of toothpaste was evaluated as dry-hardening when applying pressure using a probe, and the result was shown in Table 2. The degree of dry-hardening so that there was no mark on contents was represented as hardened, and the case that there were scratches on contents or the probe entered into contents was represented as not hardened.

Result

Examples A1-A6 and Comparative examples A1-A3 were not hardened all, and the initial viscosity was 20,000-30,000 cP, and all had improved dry-hardening phenomena when discharging and were desirable for easiness of discharging, as a pump-type toothpaste composition. However, for the dilution viscosity, it was confirmed that it was increased compared to the initial viscosity in Examples A1-A6, and it was reduced in Comparative examples A1-A3. Accordingly, it was confirmed that when applying the toothpaste composition of the present disclosure, the viscosity of the toothpaste was increased when brushing teeth, and therefore it

TABLE 2

|  | Example A1 | Example A2 | Example A3 | Example A4 | Example A5 | Example A6 | Comparative example A1 | Comparative example A2 | Comparative example A3 |
|---|---|---|---|---|---|---|---|---|---|
| Degree of hardening | Not hardened | Not hardened | Not hardened | Not hardened | Not hardened | Not hardened | Not hardened | Not hardened | Not hardened |

Experiment 2. Viscosity Measurement

The viscosity of the toothpaste compositions prepared above at 20 rpm using Brookfield Viscometer No. 5 spindle, and the result was shown in Table 3. The initial viscosity was measured after stabilizing the prepared toothpaste for 2 days, and the dilution viscosity was measured after adding purified water of 10% by weight based on the weight of the composition to the toothpaste composition stabilized for 2 days.

could provide rich feeling of use despite of dilution of the toothpaste.

II. Preparative example B of pump-type toothpaste composition

Toothpaste compositions of Examples and Comparative examples were prepared by components and weights shown in the following Table 4. Toothpaste compositions were prepared by completely distributing purified water, liquid

TABLE 3

|  | Example A1 | Example A2 | Example A3 | Example A4 | Example A5 | Example A6 | Comparative example A1 | Comparative example A2 | Comparative example A3 |
|---|---|---|---|---|---|---|---|---|---|
| Initial viscosity (cP) | 20,000 | 20,000 | 20,000 | 25,000 | 30,000 | 30,000 | 20,000 | 25,000 | 30,000 |
| Dilution viscosity (cP) | 22,000 | 28,000 | 33,000 | 50,000 | 45,000 | 55,000 | 15000 | 20,000 | 25,000 | polyol, a flavoring, a pharmaceutical agent, a surfactant, a co-bonding agent with acrylate, saccharin, a preservative, and powder components such as a surfactant, and the like and primarily mixing them, and then adding an abrasive such as silica, and the like, and a pharmaceutical agent and mixing them under a vacuum condition.

TABLE 4

| | Example B1 | Example B2 | Example B3 | Example B4 | Example B5 | Example B6 | Example B7 | Example B8 | Example B9 | Example B10 | Example B11 | Comparative example B1 | Comparative example B2 |
|---|---|---|---|---|---|---|---|---|---|---|---|---|---|
| Precipitated silica | 15 | 15 | 15 | 15 | 15 | 15 | 15 | 15 | 15 | 15 | 15 | 15 | 15 |
| Glycerin | 50 | 50 | 50 | 50 | 50 | 50 | 50 | 50 | 50 | 50 | 50 | 50 | 50 |
| Sodium lauryl sulfate | 2.2 | 2.2 | 2.2 | 2.2 | 2.2 | 2.2 | 2.2 | 2.2 | 2.2 | 2.2 | 2.2 | 2.2 | 2.2 |
| Sodium saccharin | 0.2 | 0.2 | 0.2 | 0.2 | 0.2 | 0.2 | 0.2 | 0.2 | 0.2 | 0.2 | 0.2 | 0.2 | 0.2 |
| Sodium fluoride | 0.22 | 0.22 | 0.22 | 0.22 | 0.22 | 0.22 | 0.22 | 0.22 | 0.22 | 0.22 | 0.22 | 0.22 | 0.22 |
| Vitamin E | 0.2 | 0.2 | 0.2 | 0.2 | 0.2 | 0.2 | 0.2 | 0.2 | 0.2 | 0.2 | 0.2 | 0.2 | 0.2 |
| Sodium hydroxide | 0.1 | 0.1 | 0.2 | 0.1 | 0.1 | | | | | | | | |
| Polyacrylate | 0.05 | 0.5 | 1 | 0.5 | 0.5 | | | | | | | | |
| Sodium polyacrylate | | | | | | 0.05 | 0.5 | 1 | 0.5 | 0.5 | 0.5 | 1 | |
| Sodium carboxy methyl cellulose | | | 0.5 | | | | | | 0.5 | | 0.2 | | 1 |
| Xanthan gum | 1 | 0.5 | 0.05 | | | 1 | 0.5 | 0.05 | | | 0.5 | | |
| Sodium alginate | | | | | 0.5 | | | | | 0.5 | | | |
| Flavoring | 1 | 1 | 1 | 1 | 1 | 1 | 1 | 1 | 1 | 1 | 1 | 1 | 1 |
| Purified water | 30.03 | 30.08 | 29.93 | 30.08 | 30.08 | 30.13 | 30.18 | 30.13 | 30.18 | 30.18 | 29.98 | 30.18 | 30.18 |

Experiment 1: Evaluation of Phase Stability of Prepared Toothpaste

For the toothpaste prepared as Examples B1~B11 and Comparative examples B1~B2 of Table 4, the phase stability was evaluated using evaluation criteria of phase separation, liquid separation, lumping, and uniformity of toothpaste, and the result was shown in Table 5.

TABLE 5

| | Example B1 | Example B2 | Example B3 | Example B4 | Example B5 | Example B6 | Example B7 | Example B8 | Example B9 | Example B10 | Example B11 | Comparative Example B1 | Comparative Example B2 |
|---|---|---|---|---|---|---|---|---|---|---|---|---|---|
| Viscosity (1000 cP) | Good | Good | Good | Good | Good | Good | Good | Good | Good | Good | Good | Poor | Good |

As confirmed in the Table 5, it was shown that when using only the acrylate polymer, the internal solids were agglomerated to push out liquid components in prescription, resulting in phase separation, and therefore the stability was poor.

Experiment 2: Tailing Measurement (Tailing Length Measurement)

The tailing length was evaluated by the method of measuring the residual length remaining in a discharging port after discharging pump toothpaste, and the result was shown in the following Table 6.

TABLE 6

| | Example B1 | Example B2 | Example B3 | Example B4 | Example B5 | Example B6 | Example B7 | Example B8 | Example B9 | Example B10 | Example B11 | Comparative Example B1 | Comparative Example B2 |
|---|---|---|---|---|---|---|---|---|---|---|---|---|---|
| Tailing (mm) | 4 | 3 | 2 | 2 | 2 | 4 | 3 | 2 | 2 | 2 | 2 | — | 10 |

As the result of the experiment, it was confirmed that the residual length was good but the stability was not secured and therefore it was not usable when using the acrylate polymer only; and the length was 10mm and thus at least 50% or more of tailing property of the toothpaste was reduced when not using acrylate.

Experiment 3: Evaluation of Recovery Rate of Pump Toothpaste

The strain rate and recovery rate were evaluated when applying a force of 4 Pa using a rheometer, and the result was shown in the following Table 7.

TABLE 7

| | Example B1 | Example B2 | Example B3 | Example B4 | Example B5 | Example B6 | Example B7 | Example B8 | Example B9 | Example B10 | Example B11 | Comparative Example B1 | Comparative Example B2 |
|---|---|---|---|---|---|---|---|---|---|---|---|---|---|
| Strain rate (%) | 3 | 2 | 1.5 | 2 | 2 | 3 | 2 | 1.5 | 2 | 2 | 1.3 | — | 4 |
| Recovery rate (%) | 42 | 55 | 70 | 53 | 53 | 44 | 55 | 68 | 52 | 54 | 66 | — | 33 |

Comparative example B1 had a problem in stability, and therefore it was not measured, and it was confirmed that the recovery rate was poor when using a single hydrocolloid as Comparative example B2.

Experiment 4: Measurement of Drying Speed of Pump Toothpaste

Test method: After filling toothpaste in 24 well plates, it was dried in a dry oven equipped with a fan at 60° C. for 6 hours, and then the degree of dry-hardening of toothpaste was evaluated when applying pressure using a probe (round pen), and the result was shown in the following Table 8.

The rating scale was as follows:

Hardened: The toothpaste becomes hardened to leave no marks thereon

Not hardened: There are scratches on the toothpaste or the probe enters into the toothpaste

TABLE 8

| | Example B1 | Example B2 | Example B3 | Example B4 | Example B5 | Example B6 | Example B7 | Example B8 | Example B9 | Example B10 | Example B11 | Comparative Example B1 | Comparative Example B2 |
|---|---|---|---|---|---|---|---|---|---|---|---|---|---|
| Strain rate (%) | Not hardened | Not hardened | Not hardened | Not hardened | Not hardened | Not hardened | Not hardened | Not hardened | Not hardened | Not hardened | Not hardened | — | Hardened |

Comparative example B1 had a problem in stability, and therefore it was not measured, and it was confirmed that Comparative example B2 was hardened, while the compositions of Examples B1~B11 had significantly improved dry-hardening.

The invention claimed is:

1. A pump-type toothpaste composition comprised in a pump-type container, comprising a substantially non-hydrated hydrocolloid and water, wherein the weight ratio of the substantially non-hydrated hydrocolloid and water is 0.5-10:1 (substantially non-hydrated hydrocolloid:water), wherein the hydrocolloid is xanthan gum; or the hydrocolloid is one or more selected from the group consisting of agarose, agar, cellulose, dextrin, gelatin, Japanese agar, pectin, starch, chemically modified starch, carboxymethyl cellulose, methyl cellulose, sodium carboxymethyl cellulose, hydroxypropylmethyl cellulose, hydroxymethyl cellulose, hydroxyethyl cellulose, methylhydroxypropyl cellulose, carbomer, galactomannan, glucomannan, locust bean gum, gellan gum, gum karaya, gum Arabic, gum tragacanth, guar gum, and alginate,
wherein the content of the substantially non-hydrated hydrocolloid is 3 to 6% by weight based on the total weight of the composition, and
wherein the pump-type toothpaste composition further comprises 0.1 to 50% by weight of an abrasive and 1 to 20% by weight of a foaming agent, based on the total weight of the composition.

2. The pump-type toothpaste composition according to claim 1, wherein the viscosity of the pump-type toothpaste composition is 4,000 cP to 35,000 cP.

3. The pump-type toothpaste composition according to claim 1, wherein the content of the water is less than 5% by weight based on the total weight of the composition.

4. The pump-type toothpaste composition according to claim 1, wherein the viscosity becomes increased 1.1 to 2 times when mixing 10 g of the pump-type toothpaste composition and 1 ml of water, compared to the viscosity of the composition before mixing.

5. The pump-type toothpaste composition according to claim 1, wherein the pump-type toothpaste composition is in a gel phase.

6. Pump-type toothpaste comprising the pump-type toothpaste composition according to claim 1, and a pump-type container in which the pump-type toothpaste composition is comprised.

7. A pump-type toothpaste composition comprised in a pump-type container, comprising an acrylic polymer, a hydrocolloid, and an abrasive,
wherein the acrylic polymer is uncross-linked,
wherein the hydrocolloid is substantially non-hydrated hydrocolloid,
wherein the pump-type toothpaste composition is in a gel phase, and
wherein the abrasive is selected from the group consisting of calcium monohydrogen phosphate, precipitated silica, fumed silica, hydrated silicon dioxide, colloidal silicon dioxide, silica gel, zeolite, calcium carbonate, hydrated alumina, kaolin, cellulose and a mixture thereof,
wherein the content of the substantially non-hydrated hydrocolloid is 3 to 6% by weight based on the total weight of the composition,
wherein the hydrocolloid is xanthan gum; or the hydrocolloid is one or more selected from the group consisting of agarose, agar, cellulose, dextrin, gelatin, Japanese agar, pectin, starch, chemically modified starch, carboxymethyl cellulose, methyl cellulose, sodium carboxymethyl cellulose, hydroxypropylmethyl cellulose, hydroxymethyl cellulose, hydroxyethyl cellulose, methylhydroxypropyl cellulose, carbomer, galactomannan, glucomannan, locust bean gum, gellan gum, gum karaya, gum Arabic, gum tragacanth, guar gum, and alginate, and
wherein the pump-type toothpaste composition comprises 0.05 to 1.0% by weight of the acrylic polymer.

8. The pump-type toothpaste composition according to claim 7, wherein the acrylic polymer is a polyacrylic polymer, polymethacrylic polymer, polyalkylacrylic polymer or polyalkylmethacrylic polymer.

9. The pump-type toothpaste composition according to claim 7, wherein the acrylic polymer is prepared by polymerizing one or more of monomers selected from the group consisting of acrylate, methacrylate, alkyl acrylate, alkyl methacrylate, hydroxyalkyl acrylate, hydroxyalkyl methacrylate, diethylene glycol acrylate, diethylene glycol methacrylate, acrylamide, methacrylamide, diacetone acrylamide, methylol acrylamide and methylol methacrylate.

10. The pump-type toothpaste composition according to claim 7, wherein the weight ratio of the acrylic polymer to the substantially non-hydrated hydrocolloid is 0.05 to 20.

11. The pump-type toothpaste composition according to claim 1, wherein the pump-type toothpaste composition further comprises one or more selected from an abrasive, a lubricant, a flavoring agent, a sweetener, a pharmaceutical agent, a pH adjusting agent, a preservative, a foaming agent and a whitening agent.

12. The pump-type toothpaste composition according to claim 7, wherein the pump-type toothpaste composition has at least 50% reduced length of tail of the toothpaste composition dragging from a discharge port after pumping, compared to a case of not comprising an acrylic polymer.

13. The pump-type toothpaste composition according to claim 7, wherein the pump-type toothpaste composition has a strain rate of at least 1.0% and a recovery rate of at least 40%, when applying a force of 4 Pa.

14. The pump-type toothpaste composition according to claim 7, wherein the pump-type toothpaste composition is in a gel phase.

15. The pump-type toothpaste composition according to claim 7, wherein the pump-type toothpaste composition further comprises one or more selected from an abrasive, a lubricant, a flavoring agent, a sweetener, a pharmaceutical agent, a pH adjusting agent, a preservative, a foaming agent and a whitening agent.

* * * * *